(12) United States Patent
Reddy et al.

(10) Patent No.: US 8,329,740 B2
(45) Date of Patent: Dec. 11, 2012

(54) POLYMORPHS OF SUNITINIB MALATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Thungathurthy Srinivasa Rao, Hyderabad (IN)

(73) Assignee: Hetero Research Foundation (IN)

( * ) Notice: Subject to any disclaimer, the term of this patent is extended or adjusted under 35 U.S.C. 154(b) by 15 days.

(21) Appl. No.: 13/120,453

(22) PCT Filed: Jan. 2, 2009

(86) PCT No.: PCT/IN2009/000008
§ 371 (c)(1),
(2), (4) Date: Mar. 23, 2011

(87) PCT Pub. No.: WO2010/076805
PCT Pub. Date: Jul. 8, 2010

(65) Prior Publication Data
US 2011/0306647 A1    Dec. 15, 2011

(51) Int. Cl.
*A61K 31/4015* (2006.01)
*C07D 209/34* (2006.01)

(52) U.S. Cl. .................. 514/414; 548/468

(58) Field of Classification Search .............. 548/468; 514/414
See application file for complete search history.

(56) References Cited

U.S. PATENT DOCUMENTS

| 6,573,293 B2 | 6/2003 | Tang et al. |
| 2003/0069298 A1 | 4/2003 | Hawley et al. |
| 2006/0009510 A1 | 1/2006 | Havens et al. |

FOREIGN PATENT DOCUMENTS

| WO | 0160814 A2 | 8/2001 |
| WO | 03016305 A1 | 2/2003 |
| WO | 2010/076805 A2 | 7/2010 |

OTHER PUBLICATIONS

International Search Report dated Jul. 4, 2012.

*Primary Examiner* — Shawquia Young
(74) *Attorney, Agent, or Firm* — Caesar, Rivise, Bernstein, Cohen & Pokotilow, Ltd.

(57) ABSTRACT

The present invention provides a novel crystalline form of sunitinib malate, process for its preparation and to pharmaceutical composition containing it. The present invention also provides a process for preparation of sunitinib malate crystal form I. Thus, for example, sunitinib malate was added to water, the mixture was heated to 80 deg C. to obtain a clear solution and stirred for 30 minutes at 80 deg C., slowly cooled to room temperature and the solution was subjected to freeze drying at about −90 deg C. for 8 hours to give sunitinib malate crystalline form III.

5 Claims, 2 Drawing Sheets

POLYMORPHS OF SUNITINIB MALATE

FIELD OF THE INVENTION

The present invention provides a novel crystalline form of sunitinib malate, process for its preparation and to pharmaceutical composition containing it. The present invention also provides a process for preparation of sunitinib malate crystal form I.

BACKGROUND OF THE INVENTION

Sunitinib and its salts are antineoplastic agents, which were disclosed in WO Patent Publication No. 01/60814 and U.S. Pat. No. 6,573,293. Sunitinib is known by the chemical name N-[2-(diethylamino)ethyl]-5-[(Z)-(5-fluoro-1,2-dihydro-2-oxo-3H-indol-3-ylidene)methyl]-2,4-dimethyl-1H-pyrrole-3-carboxamide. Sunitinib is represented by the following structure.

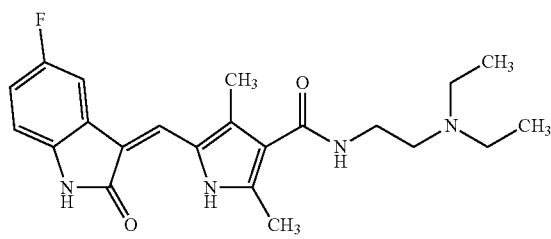

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

U.S. Patent Application No. 2003/0069298 disclosed two crystal forms, Form I (characterized by an x-ray powder diffraction patterns having peaks expressed as 2θ at 13.2, 19.4, 24.2 and 25.5 degrees) and Form II (characterized by an x-ray powder diffraction patterns having peaks expressed as 2θ at 3.0, 12.1, 14.5 and 27.7 degrees) of sunitinib malate.

One object of the present invention is to provide a novel crystalline form of sunitinib malate and a process for preparing it.

According to another object of the present invention is to provide process for preparing crystal form I of sunitinib malate.

Still another object of the present invention is to provide pharmaceutical compositions containing the novel crystalline form of sunitinib malate.

DETAILED DESCRIPTION OF THE INVENTION

In accordance with one aspect of the present invention, there is provided a novel crystalline form of sunitinib malate. The crystalline form, designated as sunitinib malate form III is characterized by peaks in the powder x-ray diffraction spectrum having 2θ angle positions at about 3.1, 9.2, 14.4, 15.0, 26.8 and 44.0±0.2 degrees. The powdered x-ray diffractogram (PXRD) of sunitinib malate crystalline form III is shown in FIG. 1.

The sunitinib malate crystalline form III may be identified and differentiated from the known polymorphs by its characteristic PXRD pattern. Thus, for example, a peak at 44.0±0.2 degrees 2θ is present in the PXRD of the sunitinib malate crystalline form III of the present invention, but is absent in the PXRD of the sunitinib malate crystal form II disclosed in the U.S. Patent Application No. 2003/0069298 A1.

In accordance with another aspect of the present invention, there is provided a process for preparing sunitinib malate crystalline form III, which comprises freeze drying an aqueous solution of sunitinib malate at −80 to −90 deg C. to obtain sunitinib malate crystalline form III.

In accordance with another aspect of the present invention, there is provided a process for the preparation of sunitinib malate crystal form I, which comprises:
a) providing a solution of sunitinib malate in dimethyl sulfoxide solvent;
b) adding an anti solvent or a mixture of anti solvents selected from acetone, methyl tert-butyl ether and isopropyl acetate; and
c) isolating sunitinib malate crystal form I.

In accordance with another aspect of the present invention, there is provided a pharmaceutical composition comprising sunitinib malate crystalline form III.

The pharmaceutical dosage form may preferably be in solid oral dosage form.

Figure 1:
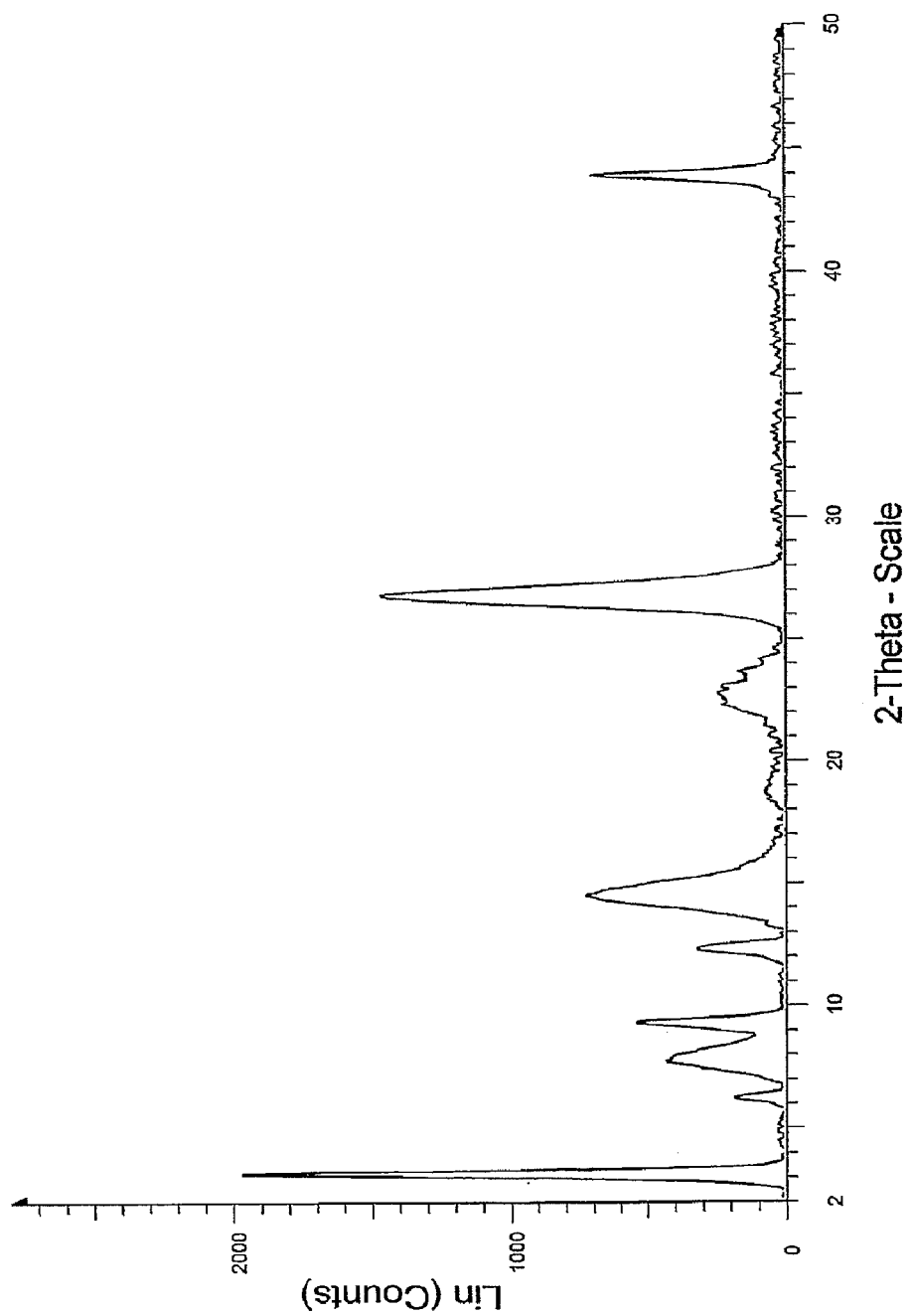
FIG. 1 is X-ray powder diffraction spectrum of sunitinib malate crystalline form III.
Figure 2:
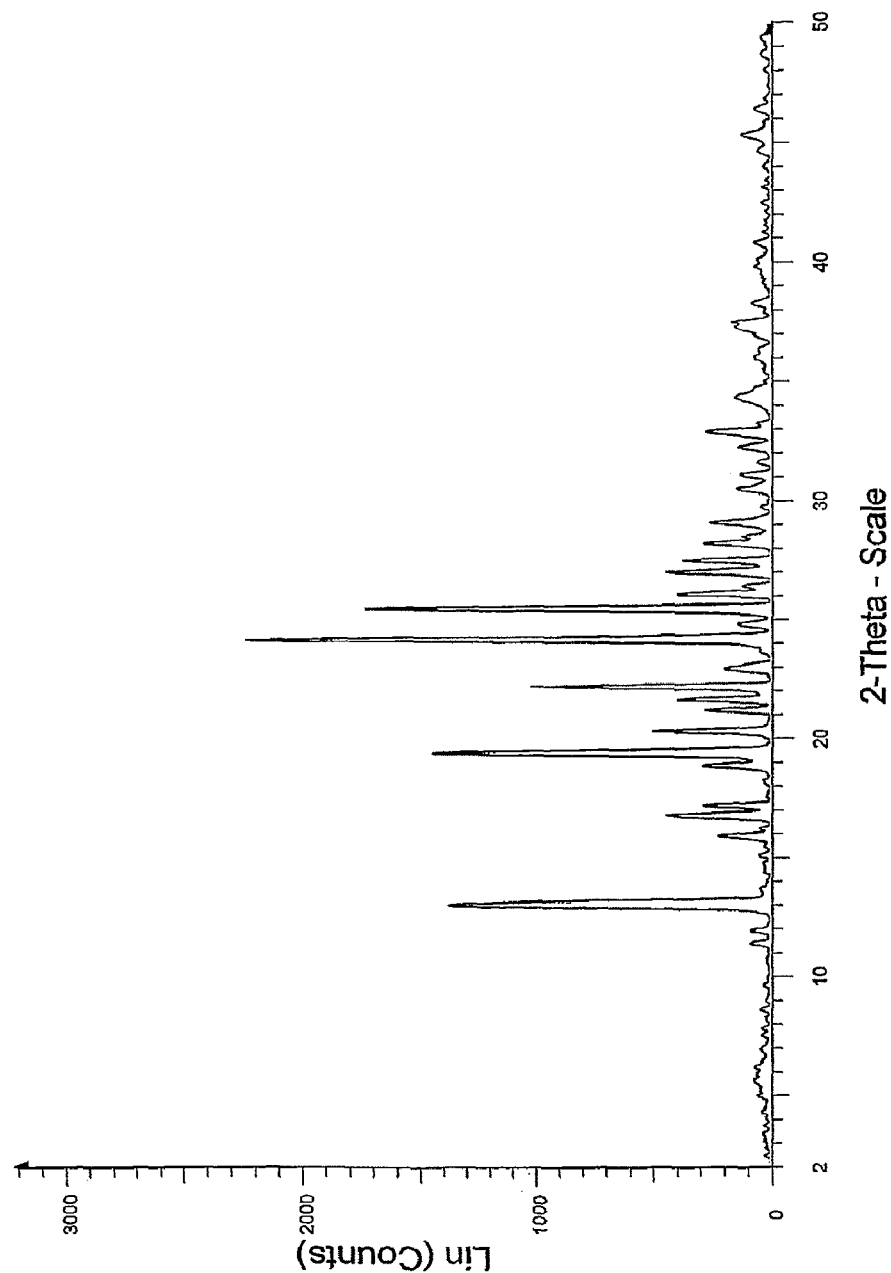
FIG. 2 is X-ray powder diffraction spectrum of sunitinib malate crystal form I.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.03 degrees to theta per step and a step of 0.5 seconds. The sample was simply placed on the sample holder. The sample was rotated at 30 rpm at a voltage 40 KV and current 35 mA.

The invention will now be further described by the following examples, which are illustrative rather than limiting.

EXAMPLES

Example 1

Sunitinib malate (5.0 gm) was added to water (75 ml), and the mixture was heated to 80 deg C. to obtain a clear solution, stirred for 30 minutes at 80 deg C. The solution was slowly cooled to room temperature. The solution was subjected to freeze drying at about −90 deg C. for 8 hours to obtain 4.7 gm of sunitinib malate crystalline form III.

Example 2

The mixture of sunitinib free base (5.0 gm), L-malic acid (1.8 gm) and water (75 ml) was heated to 80 deg C. to obtain a clear solution, stirred for 30 minutes at 80 deg C. and slowly cooled to room temperature. The solution was subjected to freeze drying at about −90 deg C. for 7 hours to obtain 6.5 gm of sunitinib malate crystalline form III.

Example 3

The mixture of sunitinib free base (5.0 gm), L-malic acid (1.8 gm) and dimethyl sulfoxide (25 ml) was heated to 80 deg C. to obtain a clear solution, stirred for 30 minutes at 80 deg C. The solution was cooled to 55-60 deg C. and acetone (150 ml) was added to the solution at 55-60 deg C., stirred for 2 hours at 55-60 deg C. The solution was further cooled to room temperature, stirred for 1 hour at room temperature and filtered. The solid obtained was washed with acetone (15 ml) and dried the solid at 60 deg C. under vacuum to obtain 5.2 gm of sunitinib malate crystal form I

Example 4

Sunitinib free base (5.0 gm), L-malic acid (1.8 gm) and dimethyl sulfoxide (25 ml) are mixed and the mixture was heated to 80 deg C. to obtain a clear solution, stirred for 30 minutes at 80 deg C. The solution was slowly cooled to room temperature and the solution was added to methyl tert-butyl ether (150 ml), stirred for 15 hours at room temperature. The solid obtained by filtration and the solid was washed with mixture of dimethyl sulfoxide (1 ml) and methyl tert-butyl ether (9 ml), and then dried at 60 deg C. under vacuum to obtain 4 gm of sunitinib malate crystal form I.

Example 5

Sunitinib free base (5.0 gm) and L-malic acid (1.8 gm) was added to dimethyl sulfoxide (25 ml), and the mixture was heated to 80 deg C. to obtain a clear solution, stirred for 30 minutes at 80 deg C. Isopropyl acetate (120 ml) was added to the solution at 80 deg C. and stirred for 2 hours at 80 deg C. The solution was slowly cooled to room temperature and stirred for 1 hour at room temperature. The contents are filtered and the solid obtained was washed with isopropyl acetate (15 ml), and then dried the solid at 60 deg C. under vacuum to obtain 5.0 gm of sunitinib malate crystal form I.

Example 6

The mixture of sunitinib free base (5.0 gm), L-malic acid (1.8 gm) and dimethyl sulfoxide (25 ml) was heated to 80 deg C. to obtain a clear solution, stirred for 30 minutes at 80 deg C. The solution was slowly cooled to room temperature and the solution was added to isopropyl acetate (72 ml). The solution was stirred for 2 hours at room temperature and filtered. The solid obtained was washed with mixture of dimethyl sulfoxide (1 ml) and isopropyl acetate (4 ml) and dried at 60 deg C. under vacuum to obtain 4.3 gm of sunitinib malate crystal form I.

We claim:

1. A sunitinib malate crystalline form III, characterized by an X-ray powder diffractogram having peaks expressed as 2θ angle positions at about 3.1, 9.2, 14.4, 15.0, 26.8 and 44.0±0.2 degrees.

2. A process for the preparation of sunitinib malate crystalline form III as defined in claim 1, which comprises freeze drying an aqueous solution of sunitinib malate at −80 degrees C. to −90 degrees C. to obtain sunitinib malate crystalline form III.

3. A process for the preparation of the sunitinib malate crystal form I, which comprises:
   a. providing a solution of sunitinib malate in dimethyl sulfoxide solvent;
   b. adding an anti solvent or a mixture of anti solvents selected from acetone, methyl tert-butyl ether and isopropyl acetate; and
   c. isolating sunitinib malate crystal form I.

4. A pharmaceutical composition comprising sunitinib malate crystalline form III of claim 1 and a pharmaceutically acceptable excipient.

5. The pharmaceutical composition as claimed in claim 4, wherein the pharmaceutical composition of sunitinib malate crystalline form III is a solid oral dosage form.

* * * * *